United States Patent [19]

Matsumoto et al.

[11] Patent Number: 5,457,192
[45] Date of Patent: Oct. 10, 1995

[54] METHOD OF MANUFACTURING D-ALLOSAN

[75] Inventors: Katsuya Matsumoto; Takashi Ebata; Hajime Matsushita, all of Yokohama, Japan

[73] Assignee: Japan Tobacco Inc., Tokyo, Japan

[21] Appl. No.: 937,847

[22] PCT Filed: Feb. 19, 1992

[86] PCT No.: PCT/JP92/00170

§ 371 Date: Oct. 21, 1992

§ 102(e) Date: Oct. 21, 1992

[87] PCT Pub. No.: WO92/14744

PCT Pub. Date: Sep. 3, 1992

[30] Foreign Application Priority Data

Feb. 21, 1991 [JP] Japan ........................... 3-77380
Jul. 3, 1991 [JP] Japan ........................... 3-162604

[51] Int. Cl.$^6$ ................... C07H 1/00; C07H 3/02
[52] U.S. Cl. ................................. 536/124; 536/1.11
[58] Field of Search ........................ 536/124, 1.11

[56] References Cited

U.S. PATENT DOCUMENTS

| | | | |
|---|---|---|---|
| 4,012,413 | 3/1977 | Hester | 540/563 |
| 4,110,533 | 8/1978 | Woodward et al. | 540/215 |
| 4,601,854 | 7/1986 | Buendia et al. | 540/29 |

OTHER PUBLICATIONS

O. Mitsunobu (1981) *Synthesis*, pp. 1–20.
J. Brimacombe et al. (1978) *Carbohydrate Research* 60:C11–C12.
P. Koll et al. (1976) *Chem. Ber.* 109:337–344 (with English Abstract).
Pratt, James W. et al., J. Am. Chem. Soc., 77, pp. 1906–1908, 1955.
Heyns, Kurt et al., Chem. Ber., 100, pp. 2317–2334, 1967.
Kruizinga, Wim H. et al., J. Org. Chem., 46, pp. 4321–4323, 1981.
Torisawa, Yasuhiro et al., Chemistry Letters, pp. 1555–1556, 1984.
Singh, U. P. et al., Canadian Journal of Chem., vol. 49, pp. 1179–1186, 1971.
Matsumoto, Katsuya et al., Heterocycles, vol. 32 No. 11, pp. 2225–2240, 1991.
Brimacombe, John S. et al., Carbohydrate Research, 40, pp. 387–390, 1975.

*Primary Examiner*—William H. Beisner
*Assistant Examiner*—Everett White
*Attorney, Agent, or Firm*—Birch, Stewart, Kolasch & Birch, Ltd.

[57] ABSTRACT

The carbonyl group at the 2-position of levoglucosenone is reduced to obtain a hydroxyl group having a β-configuration. The hydroxyl group having a β-configuration is reversed to an α-configuration, and hydroxyl groups are added at the 3- and 4-positions in a cis-α form. Finally, the protective group of the hydroxyl group at the 2-position is eliminated. The reduction of the carbonyl group at the 2-position can be performed such that the levoglucosenone is reacted with aluminum lithium hydride or sodium boron hydride in an appropriate solvent. Reversion of the hydroxyl group having a β-configuration can be performed by the Mitsunobu method or a method having a mesylation step and a step using cesium acetate. The addition of the hydroxyl groups to the 3-and 4-positions in the cis form can be performed by oxidizing the double bond across the 3- and 4-positions with an appropriate oxidizing agent. The elimination of the protective group of the hydroxyl group at the 2-position can be performed under basic conditions in accordance with normal methods. According to the method of the present invention, D-allosan can be obtained stereoselectively in high yield via a smaller number of steps than that of the conventional synthesis method.

11 Claims, No Drawings

METHOD OF MANUFACTURING D-ALLOSAN synthesizing a rare sugar, which rarely exists as a natural sugar and which is not easily accessible, in the form of a saccharide derivative with a structure applicable 8 oz to various uses.

An example of the above rare sugar is D-allose, and its 1,6-anhydride is D-allosan, represented by formula (IV) below:

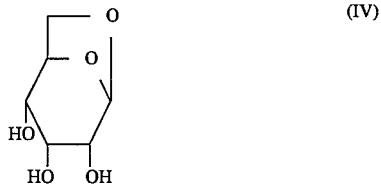

D-allosan has the same configuration of the hydroxyl groups as that of D-allose. Since hydroxyl groups at the 1- and 6-positions are combined to form an anhydro bond, thereby constituting an acetal structure, hydroxyl groups at the 1-, 5-, and 6-positions have already been selectively protected. For this reason, the structure of D-allosan as a starting material for a saccharide-containing compound is a more effective structure than that of D-allose to shorten and facilitate the introduction of a protective group of the hydroxyl group in terms of positional selectivity.

Saccharide-containing compounds containing D-allose or D-allosan as a constituent element may be employed as anti-inflammatory agents, anti-tumor agents, anemic agents, and antibiotic substances.

Various methods of manufacturing D-allosan have been attempted. A method of synthesizing D-allosan from D-ribose via D-allose by a Killiani-Fischer synthesis method (J. Pratt and N. K. Richtmyer, J. Am. Chem. Soc., 77, 1906 (1955), and a method of obtaining D-allosan by thermally decomposing corn starch to obtain 1,6-anhydro-β-D-glucopyranose (D-glucosan), oxidizing the hydroxyl group having a β-configuration at the 3-position, and reducing it to obtain the hydroxyl group having an α-configuration (K. Heyns, J. Weyer, H. Paulsen, Chem. Ber., 100, 2317 (1967)) are known.

In the former method, however, since the step of obtaining D-allose as an intermediate product is not a stereoselective reaction, D-altronic acid having an altro-configuration as a C-2 epimer of D-allose is produced. For this reason, this D-altronic acid must be separated and crystallized for elimination. Moreover, the yield is low. In the step of obtaining D-allosan by forming an anhydride having a 1,6-anhydro bond from D-allose as the intermediate product in the presence of an acid catalyst, D-allosan and D-allose as the material are equilibrated at a ratio of about 14:86 in an acidic aqueous solution, so that the material is recovered in a larger amount. For this reason, the total yield is low. That is, the total yield is about 2.4% in five steps (the total yield is 12% even if the material recovery amount in the last step is taken into consideration).

In the latter method, the yields in the first step of obtaining D-glucosan and the next step of oxidizing the hydroxyl group having a β-configuration at the 3-position of D-glucosan are as low as 25% and 14 to 19%, respectively. The last step of reducing the carbonyl group at the 3-position is not a stereoselective reaction, thereby also producing D-allosan in which the hydroxyl group is reduced in the α-configuration, and D-glucosan (i.e., the material) in which the hydroxyl group is reduced in the β-configuration. The yield of this step is as low as 30%. For this reason, the total yield in the five steps is as very low as about 1.1%.

Disclosure of Invention

It is an object of the present invention to provide a method of selectively manufacturing D-allosan in high yield.

The present inventors have made extensive studies to achieve the above object and have found a route for obtaining D-allosan stereoselectively with a higher yield than that achieved by a conventional manufacturing method, in which levoglucosenone (Carbohydrate Research, 58(1977), 78–87) known as a thermally decomposed product of a cellulose, is used as a starting material and a hydroxyl group is introduced by reduction of a carbonyl group or an oxidative addition reaction in a double bond.

That is, the method of manufacturing D-allosan according to the present invention is characterized by comprising the steps of:

(a) reducing the carbonyl group at the 2-position of levoglucosenone represented by formula (I) below to convert it into a hydroxyl group having a β-configuration, thereby obtaining a compound represented by formula (II):

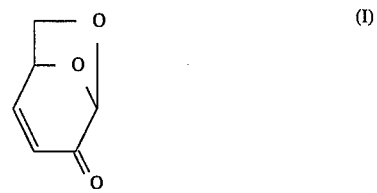

(b) reversing the hydroxyl group having a β-configuration at the 2-position of the compound obtained in step (a) and represented by formula (II) to a hydroxyl group having an α-configuration to obtain a compound represented by formula (III):

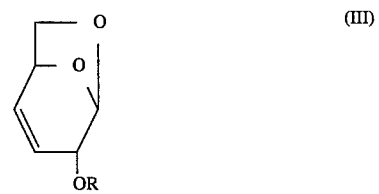

wherein R is an acyl group;

(c) adding hydroxyl groups at the 3- and 4-positions of the compound obtained in step (b) and represented by formula (III) in a cis-α-configuration; and (d) eliminating the protective group of the hydroxyl group at the 2-position in the compound represented by formula (III) to obtain D-allosan represented by formula (IV):

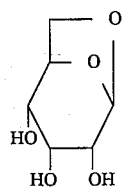

Best Mode of Carrying Out the Invention

The respective steps in manufacturing D-allosan according to the present invention will be described in detail below.

In step (a), the carbonyl group at the 2-position of levoglucosenone represented by formula (I) is reduced to convert it into a hydroxyl group, thereby obtaining a compound as a reduced product represented by formula (II). This reaction can be performed by a normal reducing method. For example, the levoglucosenone is reacted with aluminum lithium hydride or sodium boron hydride in an appropriate solvent. The yield in this step is normally 70% or more. In this reaction, a normal organic solvent or water can be used as the appropriate solvent. However, the solvent is not limited to a specific one.

In step (b), the hydroxyl group having a β-configuration at the 2-position in the compound obtained in step (a) and represented by formula (II) is reversed to a hydroxyl group having an α-configuration. A suitable reversing method is the Mitsunobu method (O. Mitsunobu, Synthesis, 1 (1981)) or a method having a mesylation step and a step using cesium acetate (W. H. Kruizinga, B. Strijtveen, R. M. Kellogg, J. Org. Chem., 46, 4321 (1981); T. Torisawa, H. Okabe, S. Ikegami, Chem. Lett., 1555 (1984)). In the Mitsunobu method, the substitution of a hydroxyl group using a relatively strong acidic compound such a carboxylic acid in the presence of diethylazodicarboxylate as an oxidizing agent and triphenylphosphine as a reducing agent. This substitution occurs from the opposite side of the hydroxyl group, and finally the hydroxyl group is reversed (at the same time the hydroxyl group is protected). According to the method using mesylation and cesium acetate, mesyl chloride or the like is reacted in an appropriate solvent such as pyridine to mesylate the hydroxyl group at the 2-position, and then the mesyl compound is reacted with cesium acetate to reverse the hydroxyl group. These techniques may be applied to the compound represented by formula (II) to convert it into the compound represented by formula (III). When the hydroxyl group is reversed according to the Mitsunobu method, the protective group R in formula (III) may be any acyl group which is normally used as a protective group and is not limited to a specific one. The yield of this step is normally 76% or more.

The double bond across the 3- and 4-positions of the compound obtained in step (b) is oxidized in the subsequent step (c) to add two hydroxyl groups in the α-configuration and the cis form. For example, this oxidation can be performed using an oxidizing agent such as osmium tetroxide or potassium permanganate in an appropriate solvent. An example of this solvent is a normal organic solvent, water, or a solvent mixture thereof. The solvent is not limited to a specific one. When osmium tetroxide is used in a catalytic amount, N-methylmorpholine N-oxide, an alkali metal chlorate, or an alkali earth metal chlorate can be used as a co-oxidizing agent.

Finally, in step (d), the protective group introduced into the hydroxyl group at the 2-position is eliminated to obtain D-allosan represented by formula (IV). In this case, all the normal conditions used to eliminate the acyl group can be used. For example, the reaction can be performed under basic conditions using an alkali hydroxide (e.g., sodium hydroxide or potassium hydroxide), an alkali carbonate (e.g., sodium carbonate or potassium carbonate), a metal alkoxide (e.g., sodium methoxide or potassium butoxide), or ammonia water. Alternatively, the above reaction may be performed under acidic conditions to prevent cleavage of the 1,6-anhydro bond. The yield in this step is normally 60% or more.

D-allosan as a reaction product represented by formula (IV) can be converted into D-allose by acid hydrolysis of the 1,6-anhydro bond in an acidic aqueous solution (U. P. Singh, R. K. Brown, Can. J. Chem., 49, 1179 (1971)).

The present invention will be described in detail by way of the examples below.

In each example, the melting point was measured using an MRK photoelectric automatic melting point measuring unit, the specific rotation was measured using a JASCO DIP-370, the IR spectrum was measured using a JASCO FT/IR-5000, and the NMR spectrum was measured using a BRUKER AM-300.

EXAMPLE 1

(Step 1) Synthesis of 1,6-anhydro-3,4-dideoxy-β-D-threo-hex-3-enopyranose (Compound (II))

2.42 g (63.8 mmol) of aluminum lithium hydride were added to 200 ml of dry ether, and a solution obtained by dissolving 7.98 g (63.3 mmol) of levoglucosenone in 130 ml of dry ether was dropped while the resultant mixture was cooled in a nitrogen-sealed ice-water bath. After dropping, the mixture was stirred at room temperature for an hour, and 4.60 g (256 mmol) of water were further dropped in the mixture. Methanol was added to the resultant reaction solution, insoluble matter in the reaction solution was filtered, and the solvent was distilled from the filtrate at a reduced pressure. The residue obtained upon distillation of the solvent was purified using a silica gel column (hexane:diethyl ether=1:1 to 1:2). The purified residue was recrystallized from a solvent mixture of hexane and diethyl ether (a mixing ratio of 4:1), thereby obtaining 5.70 g (yield: 70.3%) of 1,6-anhydro-3,4-dideoxy-β-D-threo-hex-3-enopyranose (Compound (II)).

Melting point: 65.6 to 66.4° C.
$[\alpha]_D^{25}$ −30.3° (c = 1.00, CHCl$_3$)
IR $\nu_{max}$ 3412 (br), 3050 (w), 1425 (m), 1259 (m), 1180 (m), 1125 (s), 1071 (s), 1046 (s)
$^1$H NMR (CDCl$_3$, ppm from TMS)

| | |
|---|---|
| OH; | 2.10 (1H, d, J = 12.0 Hz), |
| 1-position; | 5.52 (1H, b), |
| 2-position; | 4.34 (1H, m), |
| 3-position; | 5.72 (1H, ddd, J = 2.2, 2.2, 9.9 Hz), |
| 4-position; | 6.12 (1H, dd, J = 4.2, 9.9 Hz), |
| 5-position; | 4.67 (1H, dd, J = 4.1, 4.2 Hz) |
| 6-position; | 3.74–3.78 (1H, dd, J = 4.1, 6.6 Hz), 3.84 (1H, d, J = 6.6 Hz) |

(Step 2) Synthesis of 1,6-anhydro-3,4-dideoxy-2-O-(3,5-dinitrobenzoyl)-β-D-erythro-hex-3-enopyranose 1.92 g (15.0 mmol) of 1,6-anhydro-3,4-dideoxy-β-D-threo-hex-3-enopyranose, 7.87 g (30.0 mmol) of triphenyl phosphine, and 6.36 g (30 mmol) of dinitrobenic acid were added to 24 ml of dry THF, and a solution obtained by dissolving 5.23 g (30.0 mmol) of diethylazodicarboxylate in 24 ml of dry THF was gradually dropped in the above mixture in a nitrogen-sealed ice-water bath. The resultant solution was stirred at room temperature for 20 hours. The solvent was distilled from the reaction solution at a reduced pressure. Triphenyl phosphine oxide as a byproduct was eliminated from the residue using a silica gel column chromatograph (eluent: chloroform). The solvent was distilled from the resultant eluate at a reduced pressure, and the residue was purified using a silica gel column (hexane:ethyl acetate=4:1 to 3:1). The purified residue was recrystallized from a solvent mixture of hexane, diethyl ether, and chloroform (a mixing ratio of 1:1:1) to obtain 3.71 g (yield: 76.7%) of 1,6-anhydro-3,4-dideoxy-2-O-(3,5-dinitrobenzoyl)-β-D-erythro-hex-3-enopyranose.

---

Melting point: 154.2 to 155.3° C.
$[\alpha]_D^{25}$ −181.2° (c = 0.303, CHCl$_3$)
IR $v_{max}$ 3106 (m), 2896 (w), 1736 (s), 1630 (m),
1543 (s), 1462 (w), 1348 (s), 1270 (s),
1166 (m), 996 (m), 915 (m), 874 (m), 822
(w), 801 (w), 774 (w), 719 (s)
$^1$H NMR (CDCl$_3$, ppm from TMS)

| | |
|---|---|
| CH of 3,5-dinitrobenzoyl; | 9.19–9.26 (3H, m), |
| 1-position; | 5.72 (1H, b), |
| 2-position; | 5.07 (1H, d, J = 3.8 Hz), |
| 3-position; | 5.92 (1H, ddd, J = 2.0, 3.8, 9.9 Hz), |
| 4-position; | 6.47 (1H, dd, J = 4.7, 9.9 Hz), |
| 5-position; | 4.87 (1H, dd, J = 4.7, 4.7 Hz) |
| 6-position; | 3.76–3.82 (2H, m) |

---

(Step 3)

0.58 g (1.79 mmol) of the 1,6-anhydro-3,4-dideoxy-2-O-(3,5-dinitrobenzoyl)-β-D-erythro-hex-3-enopyranose obtained in step 2 above, 0.05 g (0.20 mmol) of osmium tetroxide, and 0.42 g (3.59 mmol) of N-methylmorpholine N-oxide were dissolved in 9 ml of a solvent mixture of acetone and water (a mixing ratio of 8:1), and the resultant mixture was stirred at room temperature for 20 hours. 5.4 ml of a 45% aqueous sodium pyrosulfite solution were added to this reaction solution, and the solvent was distilled at a reduced pressure. Hot ethanol and hot chloroform were added to the residue, thereby washing the residue. This solution was filtered, and the solvent was distilled from the filtrate at a reduced pressure.

(Step 4) Synthesis of 1,6-anhydro-β-D-allopyranose (D-allosan; Compound (IV))

120 ml of methanol and 18 ml of a 25% aqueous ammonia solution were added to the residue obtained in (step 3), and the resultant solution was stirred at room temperature for 12 hours. After the solvent was distilled at a reduced pressure, water was added to the residue, and impurities were extracted and eliminated using diethyl ether. The solution free from the impurities was purified through an Amberlite IR-120B (hydrogen cation type) cation-exchange resin and an Amberlite IRA-410 (hydroxide ion type) anion-exchange resin. The solvent was distilled from the reaction solution at a reduced pressure, and the residue was recrystallized from 2-propanol, thereby obtaining 0.12 g (yield: 39.5%) of 1,6-anhydro-βD-allopyranose (D-allosan; Compound (IV)).

---

Melting point: 174 to 176° C.
$[\alpha]_D^{25}$ −76.5° (c = 0.20, H$_2$O)
IR $v_{max}$ 3400 (br), 1338 (w), 1224 (w), 1133 (s),
1108 (s), 1029 (w), 998 (w), 971 (s),
946 (m), 915 (m), 857 (m), 779 (m), 652 (m)
$^1$H NMR (D$_2$O (OD; 4.60 ppm)):

| | |
|---|---|
| 1-position; | 5.32 ($^1$H, d, J = 2.5 Hz), |
| 2-, 3-, 4-, and 6-positions; | 3.54–3.70 (4H, m), |
| 5-position; | 4.50 ($^1$H, dd, J = 2.6, 5.4 Hz), |

13C NMR (D$_2$O, ppm from 1,4-dioxane (67.4 ppm)):
101.7, 76.9, 70.4, 70.3, 65.5, 63.7

---

EXAMPLE 2

This example is a modification of Example 1, and benzoic acid was used as the carboxylic acid in (step 2). (Step 1), (step 3), and (step 4) were performed following the same procedures as in Example 1.

(Step 2) Synthesis of 1,6-anhydro-2-O-benzoyl-3,4-dideoxy-β-D-erythro-hex-3-enopyranose 2.56 g (20.0 mmol) of 1,6-anhydro-3,4-dideoxy-β-D-threo-hex-3-enopyranose, 10.49 g (40.0 mmol) of triphenyl phosphine, and 4.88 g (40 mmol) of benzoic acid were added to 32 ml of dry THF, and a solution obtained by dissolving 6.97 g (40.0 mmol) of diethylazodicarboxylate in 32 ml of dry THF was gradually dropped in the above mixture in a nitrogen-sealed ice-water bath. The resultant solution was stirred at room temperature for 23 hours. The solvent was distilled from the reaction solution at a reduced pressure. Triphenyl phosphine oxide as a byproduct was eliminated from the residue using a silica gel column (eluent: chloroform). The solvent was distilled from the resultant eluate at a reduced pressure, and the residue was purified using a silica gel column (hexane:ethyl acetate=5:1 to 4:1). The purified residue was recrystallized from a solvent mixture of hexane and diethyl ether (a mixing ratio of 1:1) to obtain 3.48 g (yield: 74.9%) of 1,6-anhydro-3,4-dideoxy-2-O-(benzoyl)-β-D-erythro-hex-3-enopyranose.

---

Melting point: 59.6 to 61.2° C.
$[\alpha]_D^{25}$ −249.1° (c = 0.31, CHCl$_3$)
IR $v_{max}$ 2900 (w), 1717 (s), 1601 (w), 1456 (m),
1319 (m), 1247 (s), 1168 (w), 1102 (s),
1071 (m), 1023 (s), 988 (s), 905 (s),
872 (s), 801 (m), 710 (s)
$^1$H NMR (CDCl$_3$, ppm from TMS)

| | |
|---|---|
| CH of benzoyl; | 7.41–7.47 (2H, m), 7.55–7.60 ($^1$H, m), 8.07–8.11 (2H, m), |
| 1-position; | 5.68 ($^1$H, b), |
| 2-position; | 5.01 (1H, m), |
| 3-position; | 5.91 (1H, ddd, J = 1.9, 3.8, 9.8 Hz), |
| 4-position; | 6.38 (1H, ddd, J = 1.1, 4.7, 9.8 Hz), |
| 5-position; | 4.81 (1H, ddd, J = 0.7, 4.7, 4.7 Hz) |
| 6-position; | 3.73–3.80 (2H, m) |

EXAMPLE 3

This example is a modification of Example 1, and acetic acid was used as the carboxylic acid in (step 2). (Step 1), (step 3), and (step 4) were performed following the same procedures as in Example 1.

(Step 2) Synthesis of 2-O-acetyl-1,6-anhydro-3,4 -dideoxy-β-D-erythro-hex-3-enopyranose 4.15 g (32.4 mmol) of 1,6-anhydro-3,4-dideoxy-β -D-threo-hex-3-enopyranose, 17.20 g (65.6 mmol) of triphenyl phosphine, and 3.94 g (65.6 mmol) of acetic acid were added to 30 ml of dry THF, and a solution obtained by dissolving 11.42 g (65.6 mmol) of diethylazodicarboxylate in 50 ml of dry THF was gradually dropped in the above mixture in a nitrogen-sealed ice-water bath. The resultant solution was stirred at room temperature for 24 hours. The reaction solution was neutralized with a 1% aqueous sodium hydrogencarbonate solution in the ice-water bath, and the THF was distilled at a reduced pressure. The residue was extracted using diethyl ether. The extract was dried with magnesium sulfate, and the diethyl ether was distilled at a reduced pressure. Triphenyl phosphine oxide as a byproduct was eliminated from the residue using a silica gel column (eluent: chloroform). The solvent was distilled from the resultant eluate at a reduced pressure, and the residue was purified using a silica gel column (hexane:ethyl acetate=5:1 to 3:1). The purified residue was distilled at a reduced pressure (2 mmHg) to obtain 2.82 g (yield: 51.2%) of 2-O-acetyl-1,6-anhydro-3,4 -dideoxy-β-D-erythro-hex-3-enopyranose.

Boiling point: 93 to 94° C. (2 mmHg)
$[\alpha]_D^{25}$ −257.0° (c = 1.01, CHCl$_3$)
IR $v_{max}$ 1746 (s), 1234 (m), 1127 (m), 1027 (m)
$^1$H NMR (CDCl$_3$, ppm from TMS)

| | |
|---|---|
| CH$_3$CO; | 2.11 (3H, s) |
| 1-position; | 5.55 (1H, b), |
| 2- and 5-positions; | 4.75–4.78 (2H, m), |
| 3-position; | 5.79 (1H, ddd, J = 1.9, 3.8, 9.8 Hz), |
| 4-position; | 6.33 (1H, ddd, J = 1.1, 4.7, 9.8 Hz), |
| 6-position; | 3.69–3.75 (2H, m) |

EXAMPLE 4

This example is a modification of Example 1. The hydroxyl group at the 2-position of 1,6-anhydro-3,4 -dideoxy-β-D-threo-hex-3-enopyranose was reversed to the α-configuration by mesylation and by using cesium acetate. (Step 1), (step 3), and (step 4) were performed following the same procedures as in Example 1.

(Step 2)

a) Synthesis of 1,6-anhydro-3,4-dideoxy-2-O-mesyl-β -D-threo-hex-3-enopyranose 0.25 g (1.98 mmol) of 1,6-anhydro-3,4-dideoxy-β-D-threo-hex- 3-enopyranose were dissolved in 2 ml of pyridine, and 0.34 g (3.00 mmol) of mesyl chloride were dropped in this mixture under ice-water cooled conditions. The resultant solution was stirred at 0° C. for 3.5 hours and then stored in a refrigerator overnight. This reaction solution was added to 1N hydrochloric acid under ice-water cooled conditions, and extraction was performed using diethyl ether. The resultant diethyl ether solution was washed with an aqueous sodium hydrogencarbonate solution and then with an aqueous sodium chloride solution. The washed solution was dried using magnesium sulfate. The solvent was distilled at a reduced pressure, and the residue was recrystallized using a solvent mixture of hexane, diethyl ether, and ethyl acetate (a mixing ratio of 5:5:2), thereby obtaining 0.26 g (yield: 62.6%) of 1,6-anhydro-3,4-dideoxy-2-O-mesyl-β-D-threo-hex-3-enopyranose.

$^1$H NMR (CDCl$_3$, ppm from TMS):

| | |
|---|---|
| CH$_3$SO; | 3.13 (3H, s), |
| 1-position; | 5.44 (1H, b), |
| 2- and 3-positions; | 5.69–5.74 (2H, m), |
| 4-position; | 6.29 (1H, ddd, J = 1.3, 4.3, 10.4 Hz), |
| 5-position; | 4.72 (1H, dd, J = 4.2, 4.3 Hz), |
| 6-position; | 3.84 (1H, ddd, J = 1.3, 4.2, 6.7 Hz), 4.00 (1H, d, 6.7 Hz) | b) Synthesis of 2-O-acetyl-1,6-anhydro-3,4-dideoxy-β-D-erythr o-hex-3-enopyranose 0.21 g (1.00 mmol) of the above mesyl compound, 0.58 g (3.00 mmol) of anhydrous cesium acetate, and 0.26 g (1.00 mmol) of 18-crown-6-ether were added to 10 ml of dimethylformamide, and the mixture was heated under stirring at 120° C. for 19 hours. After the reaction solution was naturally cooled, it was washed with chloroform, and the solvent was distilled at a reduced pressure. The residue was purified using a silica gel column (hexane:ethyl acetate=4:1 to 3:1) to obtain 0.12 g (yield: 68.8%) of 2-O-acetyl-1,6-anhydro-3,4-dideoxy-β-D-erythro-hex-3-e nopyranose.

$^1$H NMR (CDCl$_3$, ppm from TMS):

| | |
|---|---|
| CH$_3$CO; | 2.03 (3H, s), |
| 1-position; | 5.46 (1H, b), |
| 2- and 5-positions; | 4.67–4.69 (2H, b), |
| 3-position; | 5.70 (1H, ddd, J = 1.8, 3.6, 10.1 Hz), |
| 4-position; | 6.26 (1H, dd, J = 1.1, 4.8, 10.1 Hz), |
| 6-position; | 3.62–3.69 (2H, m) |

EXAMPLE 5

This example is a modification of Example 1, and 4-nitrobenzoic acid was used as the carboxylic acid in (step 2). (Step 1), (step 3), and (step 4) were performed following the same procedures as in Example 1.

(Step 2) Synthesis of 1,6-anhydro-3,4-dideoxy-2-O-(4-nitrobenzoyl)-β-D-erythro-hex-3-enopyranose 2.56 g (20.0 mmol) of 1,6-anhydro-3,4-dideoxy-β -D-threo-hexo-3-enopyranose, 10.49 g (40.0 mmol) of triphenyl phosphine, and 6.69 g (40.0 mmol) of 4-nitrobenzoic acid were added to 32 ml of dry THF, and a solution obtained by dissolving 6.97 g (40.0 mmol) of diethylazodicarboxylate in 32 ml of dry THF was gradually dropped in the above mixture in a nitrogen-sealed ice-water bath. The resultant solution was stirred at room temperature for 41 hours. The solvent was distilled from the reaction solution at a reduced pressure. Triphenyl phosphine oxide as a byproduct was eliminated from the residue using a silica gel column (eluent: chloroform). The solvent was distilled from the resultant eluate at a reduced pressure, and the residue was purified using a silica gel column (hexane:ethyl acetate=5:1)

to obtain 4.16 g (yield: 75.1%) of 1,6-anhydro-3,4-dideoxy-2-O-(4-nitrobenzoyl)-β-D-erythro-hex-3-enopyranose. This product was recrystallized from a solvent mixture of hexane, diethyl ether, and chloroform (a mixing ratio of 1:1:1).

Melting point: 128.8 to 130.0° C.
[a]$_D^{24}$ −234° (c = 1.00, CHCl$_3$)
IR $\nu$max  3428 (w), 3112 (w), 2958 (w), 2906 (w),
             2348 (w), 1949 (w), 1719 (s), 1601 (m),
             1520 (s), 1412 (w), 1396 (w), 1352 (s),
             1323 (s), 1270 (s), 1166 (m), 1116 (s),
             1102 (s), 1019 (s), 992 (m), 973 (m),
             903 (m), 880 (s), 859 (m), 801 (m), 783
             (m), 717 (s), 576 (w), 484 (w)
$^1$H NMR (CDCl$_3$, ppm from TMS)

| CH of benzoyl; | 8.24–8.31 (4H, m), |
|---|---|
| 1-position; | 5.69 (1H, b), |
| 2-position; | 5.03 (1H, d, J = 3.9 Hz), |
| 3-position; | 5.91 (1H, ddd, J = 2.0, 3.9, 9.8 Hz), |
| 4-position; | 6.42 (1H, ddd, J = 1.1, 4.7, 9.8 Hz), |
| 5-position; | 4.42–4.85 (1H, m) |
| 6-position; | 3.74–3.81 (2H, m) |

EXAMPLE 6

This example is the modification of Example 1, and 3,5-dichlorobenzoic acid was used as a carboxylic acid in (step 2). (Step 1), (step 3), and (step 4) were performed following the same procedures as in Example 1.

(Step 2) Synthesis of
1,6-anhydro-2-O-(3,5-dichlorobenzoyl)-
3,4-dideoxy-β-D-erythro-hex-3-enopyranose 1.28 g (10.0 mmol) of 1,6-anhydro-3,4-dideoxy-β-D-threo-hex-3-enopyranose, 5.25 g (20.0 mmol) of triphenyl phosphine, and 3.80 g (20.0 mmol) of 3,5-dichlorobenzoic acid were added to 16 ml of dry THF, and a solution obtained by dissolving 3.48 g (20.0 mmol) of diethylazodicarboxylate in 16 ml of dry THF was gradually dropped in the above mixture in a nitrogen-sealed ice-water bath. The resultant solution was stirred at room temperature for 41 hours. The solvent was distilled from the reaction solution at a reduced pressure. Triphenyl phosphine oxide as a byproduct was eliminated from the residue using a silica gel column (eluent: chloroform). The solvent was distilled from the resultant eluate at a reduced pressure, and the residue was purified using a silica gel column (hexane:ethyl acetate=6:1) to obtain 2.34 g (yield: 77.7%) of 1,6-anhydro-2-O-(3,5-dichlorobenzoyl)-3,4-dideoxy-β-D-erythro-hex-3-enopyranose. This product was recrystallized from a solvent mixture of hexane, diethyl ether, and chloroform.

Melting point: 102.5 to 103.1° C.
[α]$_D^{20}$ −194° (c = 1.00, CHCl$_3$)
IR $\nu$max  3072 (w), 2974 (w), 2890 (w), 2364 (w),
             2344 (w), 1717 (s), 1572 (s), 1437 (m),
             1396 (w), 1352 (w), 1323 (w), 1263 (s),
             1145 (m), 1127 (m), 1104 (m), 1081 (w),
             1023 (s), 1002 (s), 969 (m), 909 (s),
             884 (s), 868 (s), 803 (s), 762 (s), 719
             (w), 704 (w), 659 (w), 574 (w), 478 (w),
             418 (w)
$^1$H NMR (CDCl$_3$, ppm from TMS)

| CH of benzoyl; | 7.94–7.95 (2H, m), 7.55–7.56 (1H, m), |
|---|---|
| 1-position; | 5.66 (1H, b), |
| 2-position; | 4.98 (1H, d, J = 3.8 Hz), |
| 3-position; | 5.88 (1H, dddd, J = 0.7, 2.0, 3.8, 9.8 Hz), |
| 4-position; | 6.40 (1H, dd, J = 4.7, 9.8 Hz), |
| 5-position; | 4.81–4.84 (1H, m) |
| 6-position; | 3.73–3.80 (2H, m) |

EXAMPLE 7

This example is a modification of Example 1, and 4-chlorobenzoic acid was used as the carboxylic acid in (step 2). (Step 1), (step 3), and (step 4) were performed following the same procedures as in Example 1.

(Step 2) Synthesis of
1,6-anhydro-2-O-(4-chlorobenzoyl)-
3,4-dideoxy-β-D-erythro-hex-3-enopyranose 1.28 g (10.0 mmol) of 1,6-anhydro-3,4-dideoxy-β-D-threo-hex-3-enopyranose, 5.25 g (20.0 mmol) of triphenyl phosphine, and 3.13 g (20.0 mmol) of 4-chlorobenzoic acid were added to 16 ml of dry THF, and a solution obtained by dissolving 3.13 g (20.0 mmol) of diethylazodicarboxylate in 16 ml of dry THF was gradually dropped in the above mixture in a nitrogen-sealed ice-water bath. The resultant solution was stirred at room temperature for 22 hours. The solvent was distilled from the reaction solution at a reduced pressure. Triphenyl phosphine oxide as a byproduct was eliminated from the residue using a silica gel column chromatograph (eluent: chloroform). The solvent was distilled from the resultant eluate at a reduced pressure, and the residue was purified using a silica gel column (hexane:chloroform=4:1) to obtain 2.25 g (yield: 84.3%) of 1,6-anhydro-2-O-(4-chlorobenzoyl)-3,4-dideoxy-β-D-erythro-hex-3-enopyranose.

np: 1.56
[α]$_D^{24}$ −235° (c = 1.08, CHCl$_3$)
IR $\nu$max  4082 (w), 3422 (w), 3096 (w), 3054 (w),
             2570 (w), 2370 (w), 2100 (w), 1928 (w),
             1721 (s), 1597 (s), 1491 (s), 1404 (m),
             1350 (m), 1323 (m), 1267 (s), 1172 (m),
             1104 (s), 1048 (m), 1017 (s), 996 (s),
             969 (s), 936 (m), 907 (s), 878 (s), 851
             (m), 801 (s), 760 (s), 723 (m), 708 (m),
             685 (m), 629 (w), 598 (w), 576 (w), 528
             (s), 478 (s), 453 (w)
$^1$H NMR (CDCl$_3$, ppm from TMS)

| CH of benzoyl; | 7.99–8.04 (2H, m), 7.39–7.44 (2H, m), |
|---|---|
| 1-position; | 5.54 (1H, b), |
| 2-position; | 4.99 (1H, m), |
| 3-position; | 5.89 (1H, ddd, J = 1.9, 3.9, 9.8 Hz), |
| 4-position; | 6.38 (1H, ddd, J = 1.1, 4.7, 9.8 Hz), |
| 5-position; | 4.80–4.83 (1H, m) |
| 6-position; | 3.73–3.79 (2H, m) |

EXAMPLE 8

This example is a modification of Example 1, and 3,5-dimethoxybenzoic acid was used as the carboxylic acid in (step 2). (Step 1), (step 3), and (step 4) were performed following the same procedures as in Example 1.

(Step 2) Synthesis of 1,6-anhydro-3,4-dideoxy-2-O-(3,5-dimethoxybenzoyl)-β-D-erythro-hex-3-enopyranose 1.28 g (10.0 mmol) of 1,6-anhydro-β-D-threo-hex-3-enopyranose, 5.25 g (20.0 mmol) of triphenyl phosphine, and 3.64 g (20.0 mmol) of 3,5-dimethoxybenzoic acid were added to 16 ml of dry THF, and a solution obtained by dissolving 3.48 g (20.0 mmol) of diethylazodicarboxylate in 16 ml of dry THF was gradually dropped in the above mixture in a nitrogen-sealed ice-water bath. The resultant solution was stirred at room temperature for 45 hours. The solvent was distilled from the reaction solution at a reduced pressure. Triphenyl phosphine oxide as a byproduct was eliminated from the residue using a silica gel column (eluent: chloroform). The solvent was distilled from the resultant eluate at a reduced pressure, and the residue was purified using a silica gel column (hexane:ethyl acetate=5:1) to obtain 2.45 g (yield: 83.7%) of 1,6-anhydro-3,4-dideoxy-2-O-( 3,5-dimethoxybenzoyl)-β-D-erythro-hex-3-enopyranose. This product was recrystallized from a solvent mixture of hexane and diethyl ether.

Melting point: 55.7 to 60.5° C.
$[\alpha]_D^{21}$ −167° (c = 1.03, CHCl$_3$)
IR $\nu_{max}$    3052 (w), 3010 (w), 2984 (m), 2960 (m),
2900 (m), 2844 (w), 1713 (s), 1601 (s),
1473 (s), 1429 (m), 1357 (s), 1323 (m),
1305 (s), 1228 (s), 1209 (s), 1162 (s),
1125 (m), 1100 (m), 1071 (m), 1046 (s),
1019 (s), 1000 (s), 975 (m), 928 (w),
905 (m), 874 (s), 835 (m), 801 (m), 758
(s), 723 (m), 706 (m), 669 (m), 596 (w),
576 (w), 542 (w), 497 (w), 478 (m), 439
(w)
$^1$H NMR (CDCl$_3$, ppm from TMS)

| | |
|---|---|
| CH of benzoyl; | 7.22 (2H, d, J = 2.4 Hz), 6.66 (1H, dd, J = 2.4, 2.4 Hz), |
| 1-position; | 5.68 (1H, b), |
| 2-position; | 4.98 (1H, d, J = 3.8 Hz), |
| 3-position; | 5.90 (1H, ddd, J = 1.9, 3.8, 9.8 Hz), |
| 4-position; | 6.38 (1H, ddd, J = 1.2, 4.7, 9.8 Hz), |
| 5-position; | 4.80–4.83 (1H, m) |
| 6-position; | 3.72–3.88 (2H, m) |

EXAMPLE 9

This example is a modification of Example 1, and 4-methoxybenzoic acid was used as the carboxylic acid in (step 2). (Step 1), (step 3), and (step 4) were performed following the same procedures as in Example 1.

(Step 2) Synthesis of 1,6-anhydro-3,4-dideoxy-2-O-(4-methoxybenzoyl)-β-D-erythro-hex-3-enopyranose 1.28 g (10.0 mmol) of 1,6-anhydro-β-D-threo-hex-3-enopyranose, 5.25 g (20.0 mmol) of triphenyl phosphine, and 3.04 g (20.0 mmol) of 4-methoxybenzoic acid were added to 16 ml of dry THF, and a solution obtained by dissolving 3.48 g (20.0 mmol) of diethylazodicarboxylate in 16 ml of dry THF was gradually dropped in the above mixture in a nitrogen-sealed ice-water bath. The resultant solution was stirred at room temperature for 41 hours. The solvent was distilled from the reaction solution at a reduced pressure. Triphenyl phosphine oxide as a byproduct was eliminated from the residue using a silica gel column (eluent: chloroform). The solvent was distilled from the resultant eluate at a reduced pressure, and the residue was purified using a silica gel column (hexane:ethyl acetate= 5:1) to obtain 2.06 g (yield: 78.5%) of 1,6-anhydro-3,4-dideoxy-2-O-(4-methoxybenzoyl)-β-D-eryt   hro-hex-3-enopyranose. This product was recrystallized from a solvent mixture of hexane and diethyl ether.

Melting point: 58.5 to 64.5° C.
$[\alpha]_D^{23}$ −240° (c = 0.99, CHCl$_3$)
IR $\nu_{max}$    2984 (w), 2890 (w), 2840 (w), 2348 (w),
1709 (s), 1607 (s), 1578 (w), 1514 (m),
1460 (w), 1423 (w), 1398 (w), 1354 (w),
1328 (m), 1267 (s), 1170 (s), 1127 (m),
1100 (s), 1050 (w), 1023 (s), 994 (s),
967 (m), 930 (w), 907 (m), 874 (m), 845
(m), 801 (m), 770 (m), 721 (m), 696 (m),
634 (w), 619 (w), 594 (w), 565 (w), 511
(w), 482 (m)
$^1$H NMR (CDCl$_3$, ppm from TMS)

| | |
|---|---|
| CH of benzoyl; | 8.01–8.08 (2H, m), 6.90–6.97 (2H, m) |
| 1-position; | 5.69 (1H, b), |
| 2-position; | 5.00 (1H, m), |
| 3-position; | 5.91 (1H, ddd, J = 1.9, 3.9, 9.8 Hz), |
| 4-position; | 6.38 (1H, ddd, J = 0.6, 4.7, 9.8 Hz), |
| 5-position; | 4.82 (1H, ddd, J = 0.6, 4.1, 4.7 Hz), |
| 6-position; | 3.74–3.81 (2H, m) |

As has been described above, according to the method of manufacturing D-allosan according to the present invention, D-allosan as one of the rare sugars which rarely exists naturally and which is not easily accessible can be obtained stereoselectively in high yield in accordance with a smaller number of steps than that of the conventional synthesis method. In recent years, saccharide-containing compounds functioning as physiologically active materials (typically, saccharide chains such as oligosaccharides and polysaccharides) have received a great deal of attention in the field of fine chemicals such as medical drugs and pesticides. According to the present invention, it becomes easy to supply D-allosan used as a material for synthesis of, for example, a saccharide-containing compound having D-allose partial structure introduced as one constituent unit, thereby expanding the range of synthesis studies in this field.

We claim:

1. A method of manufacturing D-allosan, comprising the steps of:

(a) reducing, by hydrogenation in a solvent, the carbonyl group at the 2-position of levoglucosenone represented by formula (I) below to convert said carbonyl group into a hydroxyl group having a β-configuration, thereby obtaining a compound represented by formula (II):

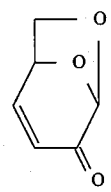
(I)

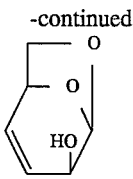 (II)

(b) reversing said hydroxyl group having a β-configuration at the 2-position of said compound obtained in step (a) represented by formula (II) to a hydroxyl group having an α-configuration to obtain a compound represented by formula (III), said reversing being carried out by employing an acidic compound in the presence of diethylazodicarboxylate and triphenylphosphine:

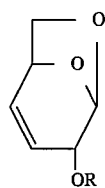 (III)

wherein R is an acyl protecting group;

(c) adding, by employing an oxidizing agent, hydroxyl groups at the 3- and 4-positions of said compound obtained in step (b) represented by formula (III) in a cis-α-configuration;

(d) eliminating said acyl protecting group R on said hydroxyl group at the 2-position in said compound represented by formula (III) by employing a member selected from the group consisting of an alkali hydroxide, an alkali carbonate, a metal alkoxide, and ammonia water, or by employing acidic conditions to obtain D-allosan represented by formula (IV):

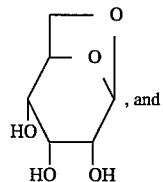 (IV), and (e) recovering said D-allosan.

2. A method of manufacturing D-allosan, comprising the steps of:

(a) reducing, by hydrogenation in a solvent, the carbonyl group at the 2-position of levoglucosenone represented by formula (I) below to convert it into a hydroxyl group having a β-configuration, thereby obtaining a compound represented by formula (II):

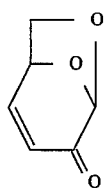 (I)

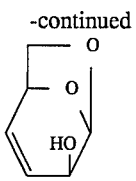 (II)

(b) reversing said hydroxyl group having a β-configuration at the 2-position of said compound obtained in step (a) represented by formula (II) to a hydroxyl group having an α-configuration to obtain a compound represented by formula (III), said reversing being carried out by mesylating said compound represented by formula (II), followed by reacting the resulting mesylated compound with cesium acetate:

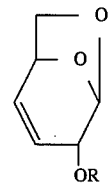 (III)

wherein R is an acyl protecting group;

(c) adding, by employing an oxidizing agent, hydroxyl groups at the 3- and 4-positions of said compound obtained in step (b) represented by formula (III) in a cis-α-configuration;

(d) eliminating said acyl protecting group R on said hydroxyl group at the 2-position in said compound represented by formula (III) by employing a member selected from the group consisting of an alkali hydroxide, an alkali carbonate, a metal alkoxide, and ammonia water, or by employing acidic conditions to obtain D-allosan represented by formula (IV):

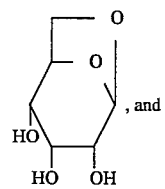 (IV), and (e) recovering said D-allosan.

3. The method of claim 1 or 2, wherein said reducing of step (a) is carried out by employing aluminum lithium hydride or sodium boron hydride.

4. The method of claim 3, wherein a solvent is a member selected from the group consisting of an organic solvent and water.

5. The method of claim 1, wherein said acidic compound of step (b) is a carboxylic acid.

6. The method of claim 5, wherein said carboxylic acid is a member selected from the group consisting of dinitrobenic acid, benzoic acid, acetic acid, 4-nitrobenzoic acid, 3,5-dichlorobenzoic acid, 4-chlorobenzoic acid, 3,5-dimethoxybenzoic acid, and 4-methoxybenzoic acid.

7. The method of claim 2, wherein said mesylating of step (b) is carried out by employing mesyl chloride in pyridine.

8. The method of claim 1 or 2, wherein said oxidizing agent of step (c) is osmium tetroxide or potassium permanganate.

9. The method of claim 8, wherein a solvent is a member selected from the group consisting of an organic solvent, water, and a mixture thereof.

10. The method of claim 8, wherein when said oxidizing agent is osmium tetroxide, a member selected from the group consisting of N-methylmorpholine N-oxide, an alkali metal chlorate, and an alkali earth metal chlorate is employed as a co-oxidizing agent.

11. The method of claim 1 or 2, wherein said alkali hydroxide is a member selected from the group consisting of sodium hydroxide and potassium hydroxide, said alkali carbonate is a member selected from the group consisting of sodium carbonate and potassium carbonate, and said metal alkoxide is a member selected from the group consisting of sodium methoxide and potassium butoxide.

* * * * *